(12) United States Patent
Thomas et al.

(10) Patent No.: US 10,130,801 B1
(45) Date of Patent: Nov. 20, 2018

(54) ELECTRONIC TRANSDERMAL CHEMICAL DELIVERY

(75) Inventors: C. Douglass Thomas, Campbell, CA (US); Peter P. Tong, Mountain View, CA (US)

(73) Assignee: IpVenture, Inc., San Jose, CA (US)

( * ) Notice: Subject to any disclaimer, the term of this patent is extended or adjusted under 35 U.S.C. 154(b) by 553 days.

(21) Appl. No.: 11/349,549

(22) Filed: Feb. 7, 2006

Related U.S. Application Data

(60) Provisional application No. 60/651,093, filed on Feb. 7, 2005.

(51) Int. Cl.
| | | |
|---|---|---|
| *A61M 37/00* | (2006.01) | |
| *A61M 31/00* | (2006.01) | |
| *A61M 5/142* | (2006.01) | |
| *A61M 5/172* | (2006.01) | |
| *A61N 1/04* | (2006.01) | |
| *A61N 1/32* | (2006.01) | |
| *A61N 1/30* | (2006.01) | |

(52) U.S. Cl.
CPC .... *A61M 37/0092* (2013.01); *A61M 5/14248* (2013.01); *A61M 5/1723* (2013.01); *A61M 31/002* (2013.01); *A61M 2005/14208* (2013.01); *A61M 2037/0007* (2013.01); *A61N 1/044* (2013.01); *A61N 1/30* (2013.01); *A61N 1/325* (2013.01)

(58) Field of Classification Search
CPC .......... A61N 1/30; A61N 1/325; A61N 1/044; A61N 1/3702; A61M 2037/0007; A61M 37/0092; A61M 31/002; A61M 2005/14208; A61M 2005/14268; A61M 5/14248; A61M 5/1723

USPC ............. 604/19, 20, 47, 173, 890.1, 21, 22, 604/65–67, 131, 501, 503, 46, 289, 304, 604/305, 306, 291; 607/152
See application file for complete search history.

(56) References Cited

U.S. PATENT DOCUMENTS

| | | | |
|---|---|---|---|
| 4,844,072 A * | 7/1989 | French et al. ................ 607/104 |
| 4,915,950 A | 4/1990 | Miranda et al. | |
| 4,931,046 A * | 6/1990 | Newman ......................... 604/20 |
| 4,942,883 A * | 7/1990 | Newman ....................... 607/152 |
| 5,084,006 A * | 1/1992 | Lew et al. ....................... 604/20 |
| 5,697,896 A * | 12/1997 | McNichols et al. ............ 604/20 |
| 5,873,850 A * | 2/1999 | Flower et al. ................... 604/20 |
| 5,876,368 A * | 3/1999 | Flower ............................ 604/20 |
| 6,098,632 A | 8/2000 | Turner et al. | |
| 6,167,302 A * | 12/2000 | Millot ............................. 604/20 |
| 6,175,763 B1 * | 1/2001 | Sorenson et al. ............... 604/20 |
| 6,219,576 B1 * | 4/2001 | Gupta et al. .................... 604/20 |
| 6,377,848 B1 * | 4/2002 | Garde et al. .................... 604/20 |
| 6,726,673 B1 * | 4/2004 | Zhang et al. .................. 604/500 |
| 6,908,448 B2 | 6/2005 | Redding, Jr. | |
| 7,182,739 B2 | 2/2007 | Kopanic et al. | |
| 7,300,409 B2 | 11/2007 | Kopanic, Jr. et al. | |

(Continued)

OTHER PUBLICATIONS

"Integral". Merriam-Webster Online Dictionary. <http://www.merriam-webster.com/dictionary/integral>.*

(Continued)

*Primary Examiner* — Lauren P Farrar

(57) ABSTRACT

Improved approaches to provide or facilitate transdermal chemical delivery to an individual are disclosed. The individual can wear an electronic transdermal chemical delivery device that delivers at least one chemical to the individual's body.

29 Claims, 1 Drawing Sheet

(56) References Cited

U.S. PATENT DOCUMENTS

| | | |
|---|---|---|
| 7,440,798 B2 | 10/2008 | Redding, Jr. |
| 2001/0020124 A1 | 9/2001 | Tamada |
| 2001/0029347 A1 | 10/2001 | Kasano |
| 2001/0056255 A1 | 12/2001 | Kost et al. |
| 2002/0038101 A1* | 3/2002 | Avrahami et al. ............... 604/20 |
| 2002/0193831 A1 | 12/2002 | Smith |
| 2003/0028170 A1 | 2/2003 | Anderson et al. |
| 2003/0176832 A1 | 9/2003 | Rossi |
| 2003/0178836 A1 | 9/2003 | Doukas et al. |
| 2003/0225360 A1 | 12/2003 | Eppstein et al. |
| 2004/0138646 A1 | 7/2004 | Walla |
| 2004/0210184 A1 | 10/2004 | Kost et al. |
| 2004/0219192 A1 | 11/2004 | Horstmann et al. |
| 2005/0143686 A1 | 6/2005 | Shevlin |
| 2005/0182389 A1* | 8/2005 | LaPorte et al. ............ 604/890.1 |
| 2005/0182398 A1 | 8/2005 | LaPorte et al. |
| 2005/0226921 A1 | 10/2005 | Kortzebom |
| 2005/0288621 A1 | 12/2005 | Phipps et al. |
| 2006/0009730 A2 | 1/2006 | Shevlin |
| 2006/0009731 A1 | 1/2006 | Wu et al. |
| 2008/0183287 A1* | 7/2008 | Ayre ........................... 623/3.28 |

OTHER PUBLICATIONS

Davison, Thomas W., "SonoPrep Ultrasonic Skin Permeation and Drug Delivery Applications," Sontra Medical Corporation, Franklin MA, Drug Delivery Companies Report Spring/Summer 2005, pp. 25-28.

Dermisonics—U-Strip Technology, http://www.dermisonics.com/technology.html, downloaded Jan. 5, 2006, 2 pages.

"Dermisonics Introduces Novel U-Wand Technology," PR Newswire, Forbes.com, Jun. 21, 2005, 4 pages.

"Prototype Developed for Ultrasonic Patch to Deliver Insulin", Penn State, University Park, PA, Oct. 22, 2002, 2 pages.

Redding, Bruce K., Jr., "A Transducer System for Ultrasonic Drug Delivery," Encapsulation Systems, Broomall, PA, Nov. 29, 2003, pp. 1-7.

Transdermal Drug Delivery, "Get the edge in a competitive environment.", 3M Drug Delivery Systems, copyright Sep. 2001, pp. 1-9 plus cover and back pages.

* cited by examiner

ELECTRONIC TRANSDERMAL CHEMICAL DELIVERY

CROSS-REFERENCE TO RELATED APPLICATION

The application claims priority to U.S. Provisional Patent No. 60/651,093, filed Feb. 7, 2005, and entitled "ELECTRONIC TRANSDERMAL CHEMICAL DELIVERY," which is hereby incorporated herein by reference.

SUMMARY OF THE INVENTION

The invention pertains to improved approaches to provide or facilitate transdermal chemical delivery to an individual. The individual can wear an electronic transdermal chemical delivery device that delivers at least one chemical to the individual's body.

The invention can be implemented in numerous ways, including as a method, system, device, apparatus, and a computer readable medium. Other aspects and advantages of the invention will become apparent from the following detailed description taken in conjunction with the accompanying drawings which illustrate, by way of example, the principles of the invention.

BRIEF DESCRIPTION OF THE DRAWINGS

The invention will be readily understood by the following detailed description in conjunction with the accompanying drawings, wherein like reference numerals designate like structural elements, and in which.

DETAILED DESCRIPTION OF THE INVENTION

Figure 1:
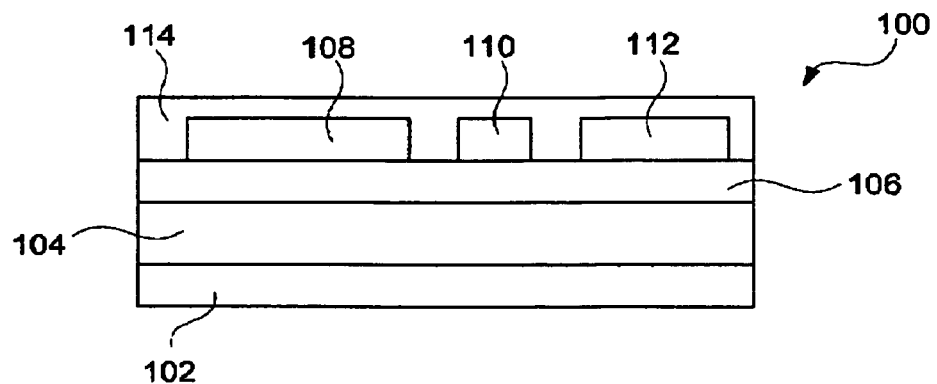
FIG. 1 is a cross-sectional view of an electronic transdermal patch according to one embodiment of the invention.

In general, a number of embodiments of the invention pertain to transdermal chemical delivery to an individual. The individual can wear an electronic transdermal chemical delivery device that delivers at least one chemical to the individual's body.

One aspect of the invention pertains to dosage adjustment for a transdermal chemical delivery device. The transdermal chemical delivery device can also be referred to as a transdermal drug delivery device. The dosage adjustment can include setting or configuring an original dosage setting and/or altering an original dosage.

In one embodiment, the dosage can be dynamically (i.e., automatically) adjusted based on feedback supplied by at least one sensor. The sensor can be integrated with the transdermal chemical delivery device. Alternatively, the sensor can wirelessly couple with the transdermal chemical delivery device. In still another embodiment, the dosage adjustment can be based on time. For example, the dosage can be adjusted in accordance with time (e.g., time of day and/or date) for providing periodic delivery of a dosage. In yet another embodiment, the dosage can be electronically programmable, either through a wired connection or a wireless connection. For example, a dosage adjustment for a transdermal chemical delivery device can be programmed by a pharmacist prior to providing the transdermal chemical delivery device to a person.

In another embodiment, the transdermal chemical delivery device can include a user input mechanism that allows the user to alter the dosage. One example of the user input mechanism is a switch.

Another aspect of the invention pertains to a transdermal chemical delivery device embodied as a patch, wherein the patch has a plurality of distinct quadrants. In each of the quadrants, the patch can supply the same or different chemical(s) to the wearer of the patch. For example, utilizing the different quadrants of a multi-quadrant patch, the patch can deliver a plurality of different chemicals simultaneously, or the patch could deliver different chemicals at different times, or the patch could deliver the same chemical at different times from different quadrants. In another example, different quadrant can carry the same chemicals but at different concentration or having different quantities to be delivered at different times.

Another aspect of the invention is to include one or more sensors within or coupled to a transdermal chemical delivery device. For example, the sensors can measure characteristics of the wearer of the patch, such as the wearer's heart rate, blood pressure, and/or body temperature; and/or characteristics of the immediate environment of the wearer, such as ambient temperature, and various other conditions.

In another aspect of the invention, through electronic or chemical mechanisms, the rate of delivery of the dosage can be normalized. For example, a newly applied patch likely tends to deliver its dosage with a greater success rate than a patch that has been applied many days ago. Although the patch applied many days ago is still effective, its rate of delivery may be substantially less than the newly applied patch. Hence, through electrical and/or chemical approaches, steps can be taken to normalize the rate of chemical delivery over an extended period of time (e.g., over the useful life of the patch).

According to another aspect of the invention, a transdermal chemical delivery device is programmable. There are various different ways to program the transdermal chemical delivery device. In one embodiment, the transdermal chemical delivery device is attached to an apparatus, such as a sheet in electronic manner. The sheet can be based on a flexible printed circuit board, such as Kapton. The sheet can include a connector for an electrical connection or a transceiver for a wireless connection to another device (e.g., computer, controller or programming system) that serves to program the one or more transdermal chemical delivery devices that are attached to the sheet. A device can couple to the connector or the transceiver so as to program the various transdermal chemical delivery devices attached to the sheet. In another embodiment, the one or more transdermal chemical delivery devices are provided in a box. The box can be coupled to a device (e.g., computer, controller or programming system) that is able to program the one or more transdermal chemical delivery devices within the box. Here, in one implementation, the various transdermal chemical delivery devices can be temporarily electrically connected to a controller. Furthermore, in the case in which a sheet is utilized, the sheet according to one embodiment can contain a conductive matrix so as to electrically couple to each of the patches attached to the sheet. With the conductive matrix, each of the patches (or even portions of a patch) can be separately addressed and programmed, or addressed and programmed in parallel. Instead of a conductive matrix, the various patches can be electrically coupled in series and programmable in a serial manner.

In another aspect of the invention, a transdermal chemical delivery device can include or couple to one or more sensors as noted above and such sensors can gather data pertaining to the wearer of the device. Here, since the transdermal chemical delivery device is typically only used for a limited period of time before being replaced, the data gathered from the one or more sensors may need to be uploaded from the transdermal chemical delivery device before the device is disposed of. In one embodiment, the transdermal chemical delivery device includes a wireless transceiver so that a controller can upload the previously gathered data in wireless manner. The data, for example, could indicate the effectiveness or performance of the transdermal chemical delivery device as worn by the person. In another example, the transdermal chemical delivery device can include a connector, such that a cable can be connected between the transdermal chemical delivery device and a host device (e.g., computer) so as to upload the gathered data. Besides a connector or a wireless transceiver, the patch can also include a memory that stores data, such as from the one or more sensors. The sensors can also store data but the memory can provide centralized storage for the data.

Another way to acquire the gathered data from the transdermal chemical delivery device is to re-attach the device to a sheet after usage. The sheet can then be coupled to an apparatus or another device (e.g., computer, controller or programming system).

According to another aspect of the invention, a housing is associated with one or more transdermal chemical delivery devices. The housing can hold or couple to a transdermal chemical delivery device. The housing can serve to store the gathered data and can later be uploaded to an apparatus or another device (e.g., computer, PDA, cell phone). The gathered data can be uploaded from the housing using a wired connection (e.g., via a connector) or using a wireless connection (e.g., via a wireless transceiver).

According to another aspect of the invention a transdermal chemical delivery device including at least one electrical component. The electrical component can vary with implementation. For example, the electrical component can be an electronic circuit. The electronic circuit can, for example, be or include a sensor, a memory, a battery, a solar cell, and/or a controller. The electronic circuit can be implemented as an integrated circuit.

In one embodiment, if the transdermal chemical delivery device includes an electrical component, such as a sensor or memory, the transdermal chemical delivery device is provided a power source, such as a battery, a solar cell, or a fuel cell, which can be coupled to, integral with or within the transdermal chemical delivery device.

According to another aspect of the invention a transdermal chemical delivery device can include a battery as well as an electronic circuit. The battery serves to provide power for the operation of the electronic circuit.

In one embodiment, the battery and the electronic circuit can be used to control the temperature of the transdermal chemical delivery device. One reason for controlling the temperature of the transdermal chemical delivery device is to influence the rate of chemical delivery from the device to the wearer.

In another embodiment, the electronic circuit is associated with a light source. In one implementation, the light source can provide ornamental lighting effects that can be powered by a power source, which can be coupled to or integral with the transdermal chemical delivery device. In still another implementation, the light source can provide an indication to the wearer of the patch. For example, the light source can provide a visual indication to the wearer. As an example, the visual indication can indicate that the currently applied patch should be replaced.

According to still another aspect of the invention, the transdermal chemical delivery device can include one or more solar cells as well as an electronic circuit. The one or more solar cells typically serve to charge a battery that is also supplied within or associated with the transdermal chemical delivery device. In the presence of light (e.g., sunshine), the solar cells can provide electronic energy that can be used to charge the battery.

The transdermal chemical delivery device can include a memory to store data that it gathers or monitors. The memory is typically a semiconductor memory. The memory can be nonvolatile memory or volatile memory depending upon implementation or application. With respect to programming the transdermal chemical delivery device, non-volatile memory, such as FLASH or EEPROM memory, might be utilized. With respect to storage of data that has been gathered, non-volatile memory might also be utilized.

As noted above, the transdermal chemical delivery device can utilize one or more sensors. The sensors can provide feedback or monitoring of the transdermal chemical delivery device itself or the wearer of such device. The feedback or monitored data can, for example, Indicate the effectiveness or rate of chemical delivery, effectiveness of the device, condition or status of the device, physical or emotional condition of the wearer, how long the device has been in use, how much chemical has been provided by the device, and/or how much chemical still remains to be provided. Additionally, electronic circuitry within the transdermal chemical delivery device can control delivery of chemical. The controlled delivery of chemical can, for example, be dependent on time or sensor information. As an example, the sensor information can pertain to physical conditions of a person utilizing the transdermal chemical delivery device. For example, if the wearer is sleeping, the rate of chemical delivery can be decreased or increased depending upon the application.

According to another aspect of the invention, the electronic circuitry within the transdermal chemical delivery device can include data communication capability, namely, wireless data communication capability. The data communication capability can be, for example, Bluetooth or WiFi compatible. For example, a doctor could wirelessly interrogate the transdermal chemical delivery device to upload data that has been gathered by the transdermal device. The doctor can then make use of this information to decide what future medications or other regiments are to be recommended to be patient. In another embodiment, the device is wirelessly coupled to a portable device carried by the wearer of the transdermal chemical delivery device. The doctor can wirelessly interrogate the delivery device through the portable device, and can remotely control the operation of the delivery device again through the portable device. Data gathered by the delivery device can be continually and wirelessly uploaded to the portable device.

In yet another aspect of the invention, an electrical component associated with the transdermal chemical delivery device can be a connector. The connector facilitates electrical connection to the transdermal chemical delivery device. In one embodiment, the connector is a USB connector. In another embodiment, the connector is a low profile connector.

FIG. 1 is a cross-sectional view of an electronic transdermal patch 100 according to one embodiment of the invention. The electronic transdermal patch 100 includes a liner layer 102, a transdermal member 104, and a substrate 106, which are arranged in a stack. In one implementation, the transdermal member 104 can be a drug-in adhesive. The substrate 106 supports electronic components 108-112. In one implementation, one of more of the electronic components 108-112 can be an integrated circuit. One of the electronic components 108-112 can also be a battery. The substrate 106 and the electronic components 108-112 can be encapsulated by a compound 114, such as a molding compound used in integrated circuit packages. The compound 114 can be considered a housing for the electronic transdermal patch 100. In one implementation, the substrate 106 can be a printed circuit board. In another implementation, the substrate 106 can be a thin film substrate, such as Kapton. In one embodiment, the side of the substrate 106 adjacent the transdermal member 104 can include an electrode pattern to assist in producing an electronic field that improves delivery of the drug or chemical from the transdermal member 104 to a person wearing the electronic transdermal patch 100. The substrate 106 can include one or more holes or opening so that the electronic components 108-112 can control and/or sense properties or conditions of the transdermal member 104.

Figure 2:
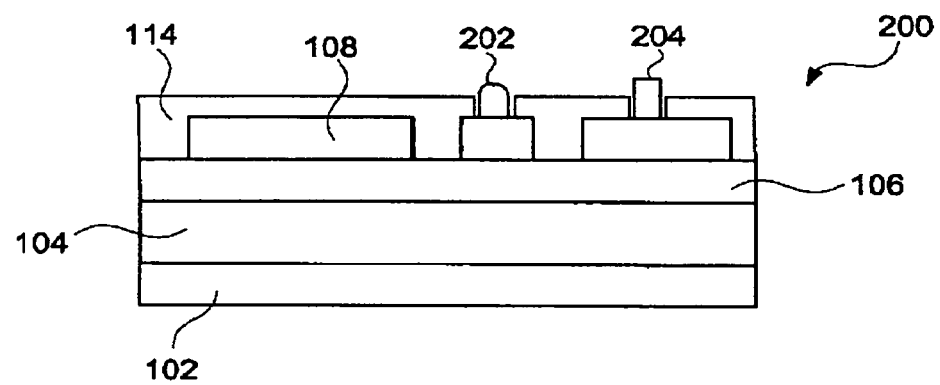
FIG. 2 is a cross-sectional view of an electronic transdermal patch according to another embodiment of the invention.

FIG. 2 is a cross-sectional view of an electronic transdermal patch 200 according to another embodiment of the invention. The electronic transdermal patch 200 is generally similar to the electronic transdermal patch 100 illustrated in FIG. 1. However, the electronic transdermal patch 200 further include a light source (e.g., LED) 202 and a switch 204. The light source 202 and the switch 204 extend through the compound 114. The light source 202 can provide feedback to the user, such as feedback as to the status of the electronic transdermal patch 200. The switch 204 can enable a user to control operation of the electronic transdermal patch 200. For example, using the switch 204, the user can turn-on/turn-off the electronic transdermal patch, turn-on an output device, acquire status information, etc.

Figure 3:
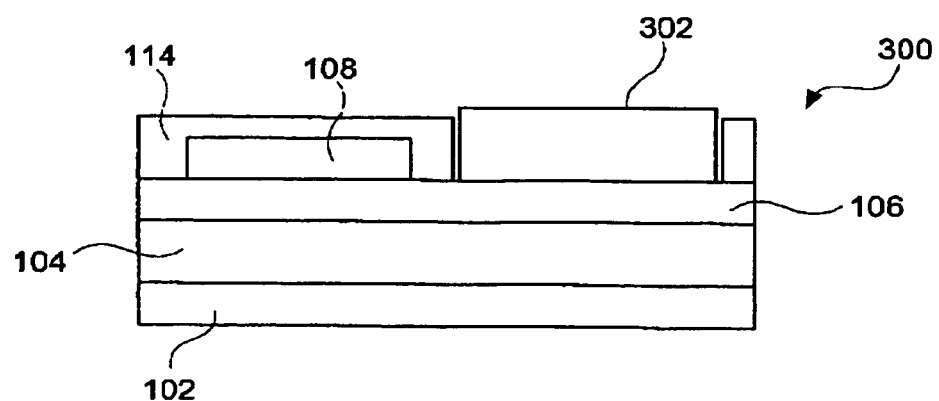
FIG. 3 is a cross-sectional view of an electronic transdermal patch according to still another embodiment of the invention.

FIG. 3 is a cross-sectional view of an electronic transdermal patch 300 according to still another embodiment of the invention. The electronic transdermal patch 300 is generally similar to the electronic transdermal patch 100 illustrated in FIG. 1. However, the electronic transdermal patch 300 further includes an output device 302. In this embodiment, the output device is a visual output device, namely, a LCD screen. The output device 302 can present output information to an interested person, such as the wearer of the electronic transdermal patch 300. The output device 302 extends through the compound 114 so as to be exposed and thus visible to the interested person.

The various aspects, embodiments, implementations or features of the invention can be used separately or In any combination.

The invention is preferably implemented by software, hardware, or a combination of hardware and software. The invention can also be embodied as computer readable code on a computer readable medium. The computer readable medium is any data storage device that can store data which can thereafter be read by a computer system. Examples of the computer readable medium include read-only memory (including FLASH and EEPROM), random-access memory, and optical data storage devices.

The many features and advantages of the present invention are apparent from the written description. Further, since numerous modifications and changes will readily occur to those skilled in the art, the invention should not be limited to the exact construction and operation as illustrated and described. Hence, all suitable modifications and equivalents may be resorted to as falling within the scope of the invention.

What is claimed is:

1. A wearable transdermal drug delivery device, comprising:
    a transdermal member containing a drug;
    a thin film substrate secured adjacent to said transdermal member, said thin film substrate having an upper side and a lower side, the lower side being adjacent and secured to said transdermal member;
    an electronic circuit, provided on the upper side of said thin film substrate, for controlling delivery of the drug to a user of said transdermal drug delivery device and for monitoring status of said transdermal drug delivery device;
    a sensor that acquires information regarding said transdermal member; and
    a wearable housing for said wearable transdermal drug delivery device, said wearable housing being configured to support at least a portion of said transdermal member, said electronic circuit, and said sensor,
    wherein the length and width of said transdermal member are not greater than the respective length and width of said wearable housing,
    wherein said electronic circuit controls the delivery of the drug using said transdermal member at least in part based on the information acquired by said sensor,
    wherein the status of said transdermal drug delivery device being monitored is at least in part dependent on the information acquired by said sensor, and
    wherein said thin film substrate includes one or more openings therein to said transdermal member to facilitate control and/or sensing of properties or conditions of said transdermal member.

2. A wearable transdermal drug delivery device as recited in claim 1, wherein the status corresponds to effectiveness, performance, or useful life of said transdermal drug delivery device.

3. A wearable transdermal drug delivery device as recited in claim 1,
    wherein the wearable transdermal drug delivery device comprises an output device, controlled by said electronic circuit, for providing at least a visual output based on the status,
    wherein said transdermal drug delivery device further comprises a switch for a user of said transdermal drug delivery device, and
    wherein said switch is used to control presentation of the output via said output device.

4. A wearable transdermal drug delivery device as recited in claim 3, wherein said transdermal drug delivery device is a patch.

5. A wearable transdermal drug delivery device as recited in claim 1, wherein said transdermal drug delivery device further comprises:
    a battery operatively connected to said electronic circuit.

6. A wearable transdermal drug delivery device as recited in claim 1, wherein said transdermal drug delivery device further comprises:
    a memory that stores drug delivery information.

7. A wearable transdermal drug delivery device as recited in claim 6, wherein said electronic circuit controls delivery of the drug to the user based on the drug delivery information.

8. A wearable transdermal drug delivery device as recited in claim 7, wherein the drug delivery information is personalized to the user.

9. A wearable transdermal drug delivery device as recited in claim 1, wherein said transdermal drug delivery device further comprises:
at least one sensor that monitors a physical condition of the user, and
wherein said electronic circuit controls the delivery of the drug to the user based in part on the monitored physical condition of the user.

10. A wearable transdermal drug delivery device as recited in claim 1,
wherein the wearable transdermal drug delivery device comprises an output device, controlled by said electronic circuit, for providing at least a visual output based on the status, and
wherein said wearable housing includes at least a first opening for said output device and a second opening for access to at least a portion of said transdermal member.

11. A wearable transdermal drug delivery device as recited in claim 1, wherein the status includes a useful life for said transdermal drug delivery device.

12. A wearable transdermal drug delivery device as recited in claim 1, wherein the status includes a performance of said transdermal drug delivery device.

13. A wearable transdermal drug delivery device as recited in claim 1, wherein the status includes an effectiveness of said transdermal drug delivery device.

14. A wearable transdermal drug delivery device as recited in claim 1, wherein the status includes a useful life and performance of said transdermal drug delivery device.

15. A wearable transdermal drug delivery device as recited in claim 1, wherein said electronic circuit is further configured to normalize a rate of drug delivery by said transdermal member over an extended period of time.

16. A wearable transdermal drug delivery device as recited in claim 1, wherein said transdermal drug delivery device further comprises:
at least one user monitoring sensor that monitors a physical condition of the user, and
wherein said electronic circuit determines whether the user is sleeping based on sensor data provided by said at least one user monitoring sensor, and controls the delivery of the drug to the user based in part on whether the user is determined to be sleeping.

17. A wearable transdermal drug delivery device as recited in claim 1,
wherein the wearable transdermal drug delivery device comprises an output device, controlled by said electronic circuit, for providing at least a visual output based on the status, and
wherein said output device produces a visual indication pertaining to a useful life for said transdermal drug delivery device.

18. A wearable transdermal drug delivery device as recited in claim 1,
wherein the wearable transdermal drug delivery device comprises an output device, controlled by said electronic circuit, for providing at least a visual output based on the status, and
wherein said output device produces a visual indication regarding replacement of said transdermal member.

19. A wearable transdermal drug delivery device as recited in claim 1, wherein performance of said transdermal member degrades over time, and wherein said electronic circuit controls delivery of the drug using said transdermal member so as to normalize rate of delivery of the drug.

20. A wearable transdermal drug delivery device as recited in claim 1, wherein said electronic circuit controls delivery of the drug using said transdermal member so as to normalize rate of delivery of the drug over time.

21. A wearable transdermal drug delivery device, comprising:
a transdermal member containing a drug;
a thin film substrate secured adjacent to said transdermal member, said thin film substrate having an upper side and a lower side, the lower side being adjacent and secured to said transdermal member;
an electronic circuit, provided on the upper side of said thin film substrate, for controlling delivery of the drug to a user of said transdermal drug delivery device and for monitoring status of said transdermal drug delivery device;
a non-volatile memory to store data pertaining to the status of said transdermal drug delivery device acquired over a period of time; and
a sensor directly coupled to at least one of said transdermal member to acquire information regarding the at least one of said transdermal member or said electronic circuit; and
a wearable housing for said transdermal drug delivery device, said wearable housing being configured to support at least a portion of said transdermal member, said electronic circuit, said non-volatile memory and said sensor,
wherein the status of said transdermal drug delivery device is at least in part dependent on the information acquired by said sensor,
wherein said electronic circuit controls the delivery of the drug using said transdermal member at least in part because based on the information acquired by said sensor, and
wherein said thin film substrate that includes one or more openings therein to said transdermal member to facilitate control and/or sensing of properties or conditions of said transdermal member.

22. A wearable transdermal drug delivery device as recited in claim 21, wherein the status of said transdermal drug delivery device includes a useful life of said transdermal member.

23. A wearable transdermal drug delivery device as recited in claim 21, wherein performance of said transdermal member degrades over time, and wherein said electronic circuit controls delivery of the drug using said transdermal member so as to normalize rate of delivery of the drug.

24. A wearable transdermal drug delivery device as recited in claim 21, wherein said electronic circuit controls delivery of the drug using said transdermal member so as to normalize rate of delivery of the drug over time.

25. A wearable transdermal drug delivery device, comprising:
a transdermal member containing a drug; and
a thin film substrate secured adjacent to said transdermal member, said thin film substrate having an upper side and a lower side, the lower side being adjacent and secured to said transdermal member;
an electronic circuit, provided on the upper side of said thin film substrate, coupled to said transdermal member, said electronic circuit operates to at least (i) control delivery of the drug to a user of said transdermal drug delivery device, and (ii) monitor temperature of said transdermal member, wherein the control of the delivery of the drug by said electronic circuit is dependent upon the temperature of said transdermal member being monitored, wherein said electronic circuit is further monitors effectiveness or performance of said transdermal drug delivery device, wherein said transdermal drug delivery device further comprises:
   a non-volatile memory that stores data pertaining to the effectiveness or performance of said transdermal drug delivery device gathered over a period of time, wherein the data pertaining to the effectiveness or performance is accessible by another electronic device for transfer of at least a portion of the data to the another electronic device, and wherein said transdermal drug delivery device is a wearable device having a housing, and, at least while being worn, the housing integrally includes said transdermal member, said electronic circuit and said non-volatile memory, and wherein the lower side of said thin film substrate includes an electrode pattern that is adjacent said transdermal member.

26. A wearable transdermal drug delivery device as recited in claim 25, wherein said electronic circuit further operates to (iii) control the temperature of said transdermal member.

27. A wearable transdermal drug delivery device, comprising:
   a transdermal member containing a drug; and
   a thin film substrate secured adjacent to said transdermal member, said thin film substrate having an upper side and a lower side, the lower side being adjacent and secured to said transdermal member;
   an electronic circuit, provided on the upper side of said thin film substrate, coupled to said transdermal member, said electronic circuit operates to at least control delivery of the drug to a user of said transdermal drug delivery device, wherein said electronic circuit further monitors effectiveness or performance of said transdermal drug delivery device, wherein said transdermal drug delivery device further comprises:
   a non-volatile memory to store data pertaining to the effectiveness or performance of said transdermal drug delivery device gathered over a period of time, wherein the data pertaining to the effectiveness or performance is accessible by another electronic device for transfer of at least a portion of the data to the another electronic device, wherein said transdermal drug delivery device is a wearable device having a housing, and, at least while being worn, the housing integrally includes said transdermal member, said electronic circuit and said non-volatile memory, and wherein the lower side of said thin film substrate includes an electrode pattern that is adjacent said transdermal member.

28. A wearable transdermal drug delivery device as recited in claim 27, wherein said transdermal drug delivery device further comprises:
   a sensor to acquire information regarding said transdermal member.

29. A wearable transdermal drug delivery device as recited in claim 28, wherein the status of said transdermal drug delivery device being monitored is at least in part dependent on the information acquired by said sensor.

* * * * *